United States Patent [19]

Adachi et al.

[11] Patent Number: 5,403,719

[45] Date of Patent: Apr. 4, 1995

[54] METHOD FOR ASSESSING PROGNOSIS OF A PATIENT UNDERGOING THERAPY FOR CANCER

[75] Inventors: Masakazu Adachi, Takasaki; Masahiro Nakatani, Shiga; Seiichirou Honda, Yokohama, all of Japan

[73] Assignees: Japan Immuno Research Laboratories Co., Ltd., Takasaki; Sekisui Kagaku Kogyo Kabushiki Kaisha, Osaka, both of Japan

[21] Appl. No.: 257,572

[22] Filed: Jun. 9, 1994

Related U.S. Application Data

[63] Continuation of Ser. No. 829,525, Feb. 3, 1992, abandoned, which is a continuation of Ser. No. 609,120, Nov. 2, 1990, abandoned, which is a continuation of Ser. No. 282,216, Dec. 9, 1988, abandoned.

[30] Foreign Application Priority Data

Dec. 10, 1987 [JP] Japan ................................ 62-313027
Oct. 24, 1988 [JP] Japan ................................ 63-267947

[51] Int. Cl.⁶ .................... C12Q 1/02; C12N 1/00; G01N 33/48; A61M 35/00
[52] U.S. Cl. ............................................. 435/29; 435/4; 435/243; 436/64; 210/645; 604/4; 604/5; 604/6
[58] Field of Search ................. 435/2, 179, 180, 803, 435/243, 4, 29; 436/63, 169, 177, 178, 66, 67, 64; 422/69; 210/645, 678, 692; 604/4, 5, 6

[56] References Cited

U.S. PATENT DOCUMENTS

| H600 | 3/1989 | Tanaka et al. ........................ 422/56 |
|---|---|---|
| 302,271 | 1/1975 | Hargest . |
| 3,682,596 | 8/1972 | Stone et al. ........................ 436/178 |
| 3,892,236 | 7/1975 | Djerassi ................................ 604/6 |
| 4,255,267 | 3/1981 | Hoehn et al. ........................ 210/678 |
| 4,256,588 | 3/1981 | Hoehn et al. ........................ 210/692 |
| 4,596,657 | 6/1986 | Wisdom . |
| 4,678,757 | 7/1987 | Rapkin et al. ........................ 436/169 |
| 4,685,900 | 8/1987 | Honard et al. ........................ 604/5 |
| 4,687,808 | 8/1987 | Jarrett et al. ........................ 604/4 |
| 4,692,411 | 9/1987 | Ghose ................................ 604/4 |
| 4,808,315 | 2/1989 | Manabe et al. ........................ 210/645 |

FOREIGN PATENT DOCUMENTS

| 2477882 | 9/1981 | France . |
|---|---|---|
| 0136230 | 10/1980 | Japan ................................ 210/692 |
| 5136230 | 10/1980 | Japan ................................ 210/692 |
| 8002805 | 12/1980 | WIPO ................................ 210/645 |

OTHER PUBLICATIONS

Davison et al.; "Effects of dietary corticosterone on peripheral blood lymphocytes and granulocytes populations in immature domestic fowl" Res. Vet. Sci, 34(2), 236–9, Mar. 1983.

Seiverd, Charles E.; "Hematology For Medical Technologists" 4th Ed., Lea & Febiger, Pa., 1975, pp. 89–90.

Patent Abstracts of Japan, vol. 6, No. 73 (C–101) 08 May 1982, & JP–A–57 11920 (Asahi Kasei Kogyo K.K.) 21 Jan. 1982, entire document.

World Pat. Index Latest Database, Derwent Publications LH, London, G.B. DW 8449, class A96 B04, Abstract No. 84–304082/49 & JP–A–59189860 (Asahi Chemical Ind. K.K.).

Patent Abstract of Japan, vol. 3, No. 72 (C–49) 21 Jun. 1979, & JP–A–54 46812 (Asahi Kasei Kogyo K.K.) 13 Apr. 1979, entire document.

*Primary Examiner*—Robert J. Warden
*Assistant Examiner*—Christopher Y. Kim
*Attorney, Agent, or Firm*—Oblon, Spivak, McClelland, Maier & Neustadt

[57] ABSTRACT

A method for assessing the prognosis of a patient undergoing therapy for cancer by measuring the granulocyte/lymphocyte ratio of the patient's blood and comparing the ratio to a normal range of 1.6-0.6. The prognosis is considered improved when the G/L value is within the range as compared to when it is greater than the same.

1 Claim, 10 Drawing Sheets

METHOD FOR ASSESSING PROGNOSIS OF A PATIENT UNDERGOING THERAPY FOR CANCER

This application is a continuation of application Ser. No. 07/829,525, filed on Feb. 3, 1992, now abandoned, which is a continuation of application Ser. No. 07/609,120, filed on Nov. 2, 1990, now abandoned, which is a continuation of application Ser. No. 07/282,216, filed on Dec. 9, 1988, now abandoned.

BACKGROUND OF THE INVENTION

1) Field of the Invention

This invention relates to a method for the removal of granulocytes from blood and also to an apparatus suitable for use in the practice of the method. In particular, this invention is concerned with method and apparatus for removing granulocytes from blood taken out of a human body and then returning the treated blood to the same human body.

2) Description of the Related Art

The significant technical improvements in the screening and diagnosis of cancers in recent years, especially, the provision of new diagnostic techniques relying upon various images and permitting serum-dependent diagnoses has made a considerable contribution to the field of therapy.

These days, however, there is no satisfactory means or standard for making it possible to correctly grasp the conditions or pathema of a cancer patient per se, namely, a cancer-bearing host. As a method in use, there is nothing closer than the method relying upon the performance status (ECOS-PS) classification which is based on the grasp of usual physiological conditions through changes in hemogram or the like and the subjective symptom of the patient himself.

It has been clinically pointed out in full that even when a similar treatment is applied to cancer patients whose definite diagnosis has been made and who are not different as far as conventional background factors are concerned, their therapeutic results, prognoses and the like may differ significantly. No report has yet been known even on means for seizing differences in the conditions of the hosts, to say nothing of such factors.

Under the above-mentioned circumstances, the present inventor has found that the ratio in number of granulocytes (G) to lymphocytes (L) (hereinafter abbreviated as "G/L ratio") in the blood of a cancer patient serves as a marker which correctly reflects the conditions or pathema of the host. Namely, it has been found that changes in the G/L ratio correctly reflect the therapy sensitivity (refractoriness) and prognosis of a cancer bearing host and a cancer patient with a G/L ratio maintained within a normal range set based on normal subjects is sensitive to therapy, in other words, has good treatment results and the course and prognosis of the cancer are good.

The higher the G/L ratio, the more serious the treatment results, course and prognosis. In the case of a cancer patient immediately before his death, an abrupt increase in the G/L ratio is observed.

Accordingly, the G/L ratio of a cancer patient is the aforementioned desirable host marker and is believed to become an effective means for judging changes in pathema of a cancer bearing patient in the field of clinical therapy of a cancer.

SUMMARY OF THE INVENTION

From the above results, it was gathered that lowering of the G/L ratio by selective removal of granulocytes from the blood of a cancer patient gives good influence to the treatment of his cancer.

A granulocyte removing apparatus suitable for use for such purposes has also been considered accordingly.

It has also been found that the use of a substance, whose contact angle to water falls within a specific range, as granulocyte-adsorbing beads permits selective removal of granulocytes without substantial loss of the other blood cell components, plasma components, etc.

The present invention has been completed on the basis of the above findings.

An object of this invention is therefore to provide a method for the removal of granulocytes from blood, which comprises bringing the blood into contact with beads having higher affinity for granulocytes than for lymphocytes.

Another object of this invention is to provide a granulocyte removing apparatus, which comprises:
- a granulocyte-adsorbing portion enclosing therein beads having higher affinity for granulocytes than for lymphocytes;
- a blood inflow port for causing blood to flow into the adsorbing portion; and
- a blood outflow port for allowing the blood, which has flowed in the adsorbing portion, to flow out of the adsorbing portion.

A further object of this invention is to provide method and apparatus for removing granulocytes from blood taken out of a human body and then returning the treated blood to the same human body.

The method and apparatus of this invention can be used to continuously lower the granulocyte level of a cancer patient by external circulation. Use of the method of this invention makes it possible to favorably improve the G/L ratio of a cancer patient which generally has an abnormally high value, namely, whereby the G/L ratio can be lowered to or toward its normal level. Such a patient can respond to various cancer treatments, good treatment results are available, and good prognosis is also assured.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

No particular limitation is imposed on the material of beads having higher affinity for granulocytes than for lymphocytes (hereinafter called simply beads), which is used in the method and apparatus of this invention, so long as it does not affect adversely on the blood which is to be brought into contact with the beads. It is however preferable to use a beads whose contact angle to water falls within a range of 55°–95°.

Beads with a contact angle within the above range can achieve sufficient adsorption of granulocytes, whereby effective removal of granulocytes is feasible. Moreover, it can minimize adsorption of other blood cell components, plasma components and serum components and is hence superior in the selective adsorption of granulocytes. Specifically, polystyrene, cellulose acetate, nylon such as 6-nylon or 11-nylon, polytrifluoroethylene and polyethylene terephthalate are suitable in particular. Needless to say, two or more of these beads may be used in combination.

Here, the term "contact angle" means an angle formed by a free surface of a stationary liquid and a solid surface at a point where the free surface is in contact with the solid surface. The angle located inside the liquid is employed.

Contact angles of principal carriers to water may be summarized as shown in Table 1.

TABLE 1

| Material | Contact angle to water (°) |
| --- | --- |
| Cellulose acetate | 60 |
| Polystyrene | 91 |
| Nylon | 70 |
| Polytetrafluoroethylene (TEFLON) | 108 |
| Polytrifluoroethylene | 92 |
| Polyethylene terephthalate | 81 |
| Polyethylene | 94 |
| Polyvinyl chloride | 87 |
| Polyvinyl alcohol | 36 |
| Acrylic resin | 54 |
| Glass | 8 |
| Ethylcellulose | 64 |

The shape and size of the beads are also optional and no particular limitation is imposed thereon. They are, however, preferable to have a size distinguishable from blood cells and a shape having a large contact area with the blood to be brought into contact therewith, namely, permitting efficient contact. For example, the beads may take the form of beads having a diameter of about 0.1–10 mm.

It is particularly preferred to use beads whose diameter ranges from 0.5 mm to 7 mm. When a granulocyte-adsorbing portion (for example, column) with beads packed therein is used, an unduly small particle size of the beads requires a high pressure for the transportation of blood. Use of such a high pressure may in turn lead to a potential problem of hemolysis. In addition, such a high pressure may result in another potential problem that thrombi would be formed to induce blocking of the granulocyte-adsorbing portion and hence to reduce the flow rate of the blood through the granulocyte-adsorbing portion. If the particle size is too large on the other hand, the surface area per unit volume is reduced and the efficiency of the processing is lowered accordingly.

Beads can be obtained by molding a thermoplastic resin such as polystyrene, cellulose acetate, nylon, polytrifluoroethylene or polyethylene terephthalate in accordance with a known molding technique such as injection or extrusion. The particle size could be controlled, as needed, by polishing them after their formation. Beads having a particle size smaller than 1 mm can be produced by a conventional polymerization process such as suspension polymerization. On the other hand, glass beads can be formed from molten glass.

The above beads may preferably be made of such material that has low affinity for other blood cell components and plasma component to avoid their simultaneous adsorption. It is however not absolutely necessary to limit the material of the beads to such a material, since such components may be replenished.

A granulocyte-removing apparatus according to one embodiment of this invention will next be described with reference to FIG. 1 of the accompanying drawings.

Figure 1:
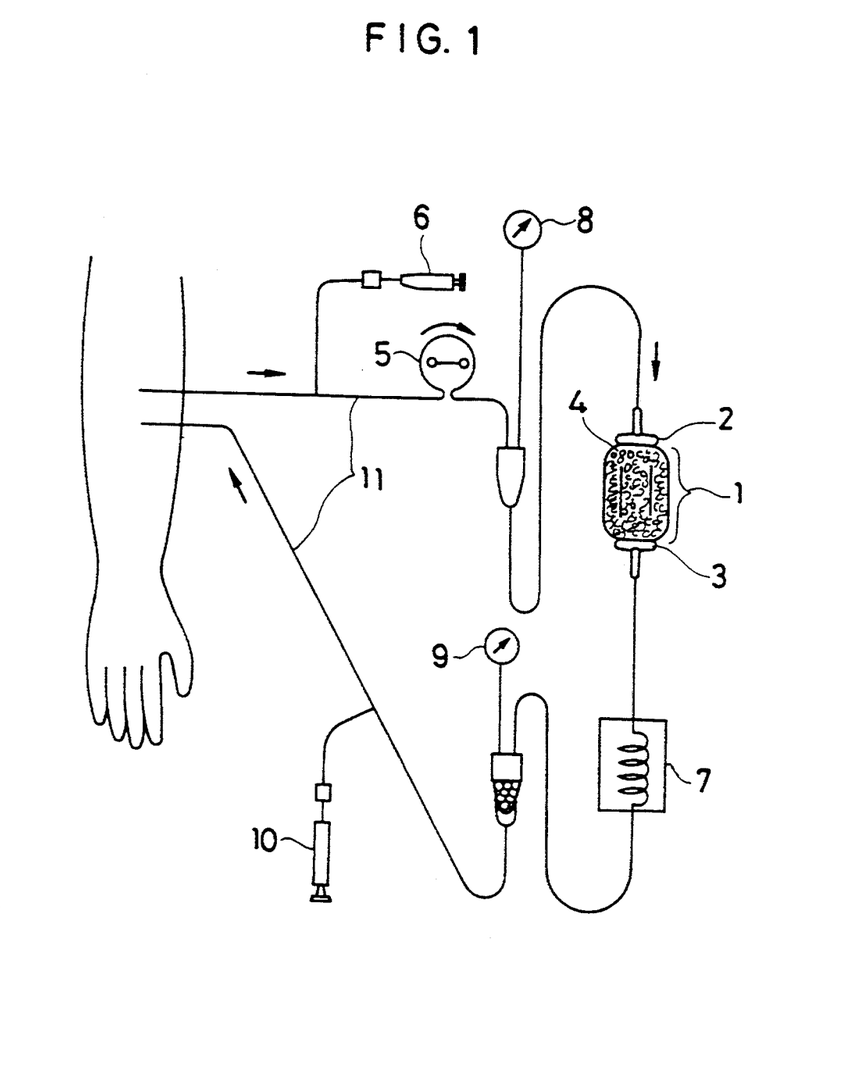
FIG. 1 schematically illustrates a granulocyte removing apparatus according to one embodiment of this invention.

In FIG. 1, numeral 1 indicates a granulocyte-adsorbing portion in which beads 4 having a contact angle of 55°–95° to water is packed.

At one end of the adsorbing portion 1 with the beads packed therein, a blood inflow port 2 is provided to cause blood, which is to be treated (patient's blood of a high G/L ratio), to flow into the adsorbing portion. On the other end, a blood outflow port 3 is provided to allow the blood to flow out of the absorbing portion subsequent to adsorption and removal of its granulocytes owing to its contact to the beads. In addition, a filter may be provided at each of the blood inflow port 2 and blood outflow port 3 of the adsorbing portion 1 in order to prevent the beads from flowing out of the adsorbing portion 1.

The apparatus of this invention can be used in accordance with the conventional plasma exchange therapy so that granulocytes are continuously removed by external circulation to improve the G/L ratio. As transportation means, the apparatus is also equipped with pipings 11 made of a nontoxic material such as silicone rubber or polyvinyl chloride and a blood pump 5.

The circulation loop for the blood fed out from the blood outlet port may be provided with arterial pressure gauge 8 and venous pressure gauge 9 to confirm that the circulation of the blood is effected without problems, a drug feed port 6 for adding a drug for the prevention of coagulation of the blood, for example, heparin, another drug feed port 10 for adding a drug to neutralize the action of such an anticoagulant, for example, protamine, a heater 7 for raising the blood temperature which would otherwise drop, etc. It is also feasible to provide a conventional detector for monitoring the hemogram of the recirculating blood and a blood component replenishing device for supplementing deficiency of any blood component or components other than granulocytes, which may be caused by the practice of the method of this invention.

As blood component or components for such replenishment, it is possible to use, for example, blood component or components for component transfusion.

The principal feature of the method and apparatus of this invention resides in that blood is brought into contact with beads and granulocytes are adsorbed on the beads to remove granulocytes from the blood or to lower the concentration of granulocytes in the blood. Accordingly, the G/L ratio is lowered and the blood is thus recovered in a state permitting its return into the organism. No suggestion has heretofore been made on a means for enabling removal of granulocytes from blood or reduction of the granulocyte level in blood, to say nothing of the method featuring contact to such a beads. Gravity centrifugation making use of a reagent in the form of a high-density layer is known as a method for removing granulocytes from blood. This method, however, does not provide blood having a lowered granulocyte level. Even if reconstitution is feasible, the processed blood by this method is still accompanied by problems for its return to the organism.

The method and apparatus of this invention can be used to continuously lower the granulocyte level of a cancer patient by external circulation. No particular limitation is, however, imposed on the manner of the method and/or apparatus. For example, the method and apparatus of this invention can be applied to blood taken out of the body, whereby granulocytes are removed or reduced in level to provide blood having a lowered granulocyte level.

Use of the method of this invention makes it possible to favorably improve the G/L ratio of a cancer patient which generally has an abnormally high value, namely, whereby the G/L ratio can be lowered to or toward its normal level.

Here, G/L ratio as a host marker is described in detail. Its normal range can be defined as about 1.6 ±0.6. A cancer patient having such a G/L ratio can be judged to be in a good state as a host.

Such a patient can respond to various cancer treatments, good treatment results are available, and good prognosis is also assured.

On the other hand, a cancer patient having a G/L ratio greater than the normal range can be judged, as a host, to be under undesirable conditions. Such a patient is refractory to therapy and the prognosis is bad. An increase in G/L ratio reflects worsening of conditions of the host, so that a very high value is exhibited before the patients dies.

G/L ratio is, therefore, an extremely useful marker for the grasp of conditions of a cancer patient as a host.

It is also extremely useful for the treatment of a cancer patient to positively correct his G/L ratio either to or toward the normal range.

Incidentally, the counting methods of G, L and white blood cells (G+L) have all been known. It is hence feasible to follow any conventional counting methods. Further, automatic cell counters have also been marketed. They can, therefore, be counted with ease.

This invention will hereinafter be described in detail by the following Examples. It should however be borne in mind that the present invention is by no means limited to or by them.

In the following Examples, the calculation of each G/L ratio was conducted by counting G and L by an automatic analyzer ("Sysmex E-4000", trade name; manufactured by Toa Medical Electronics Inc.) unless otherwise specifically indicated.

EXAMPLE 1

G/L Ratio of Normal Subject:

Determined were the G/L ratios of 51 normal subjects (30 male subjects and 21 female subjects), whose ages ranged from 22 to 52, fell within a range of 1.6±0.6. This range was hence adopted as a normal range.

EXAMPLE 2

G/L Ratio of Patient Group

Determined were the G/L ratios of stomach polyposis/gastric scar ulcer patients (n=16) and hepatic cirrhosis/hepatitis patients (n=16) as non-cancer patients and those of cancer patients (data 3 months before death: n=22; data 2 months before death: n=30; data 1 month before death: n=50). Results are shown in FIG. 2.

Figure 2:
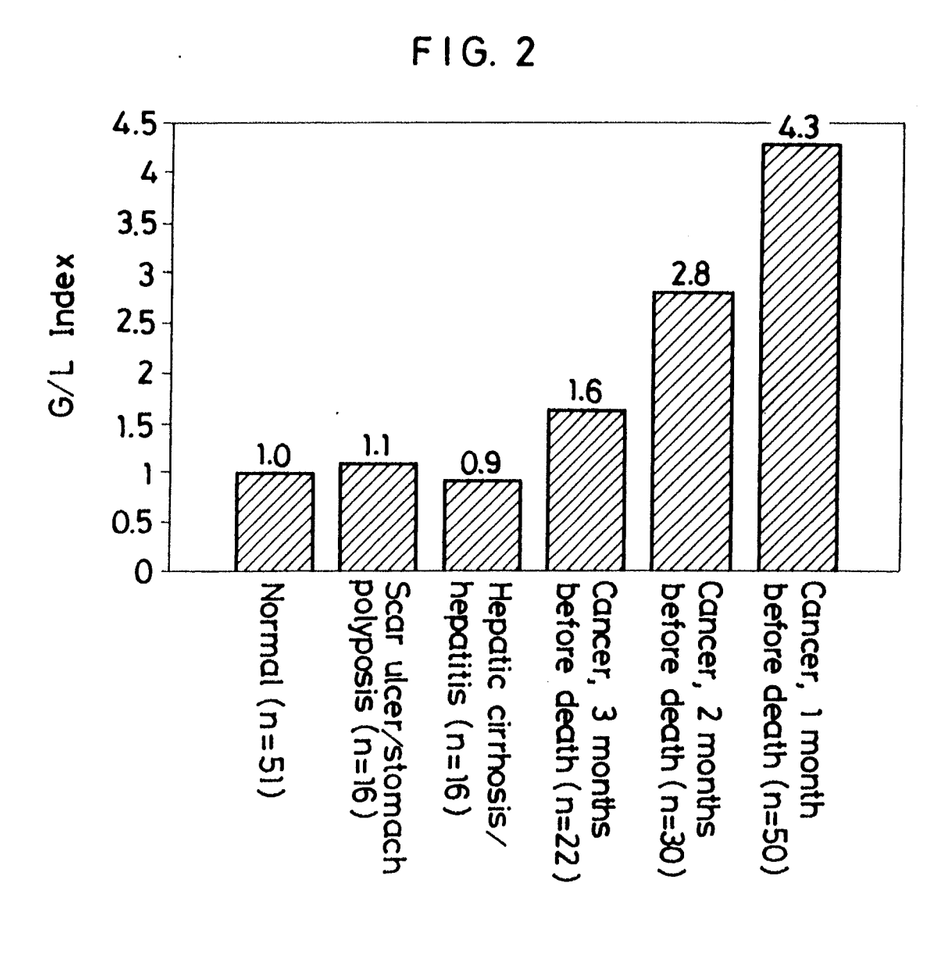
FIG. 2 diagrammatically depicts variations in G/L ratio of patients of various diseases.

In FIG. 2, the axis of ordinates indicates G/L ratios (G/L indices) when calculation was made assuming that the average (1.6) of the G/L ratios of the normal subjects is 1.0. Various groups are plotted along the axis of abscissas. It is understood from FIG. 2 that G/L ratio increases as the conditions of a cancer-bearing host are aggravated.

EXAMPLE 3

Prognosis and G/L Ratio of Cancer Patient:

A study was conducted on the prognosis of Group A, which consisted of 17 advanced cancer patients having a G/L ratio not greater than 3.0, and that of Group B which consisted of 27 advanced cancer patients having a G/L ratio greater than 3.0. By the way, no significant difference ($X^2$-test) was observed between those two groups in any one of background factors which included age (21–90 years old), cancer species (gastric cancer, uterine cancer, large bowel cancer, esophageal carcinoma, mastocarcinoma, lung cancer, pancreatic cancer, uterocervical cancer, angiosarcoma, paranasal sinus cancer, ovarian cancer, bladder cancer and gallbladder cancer as well as performance status (P.S.).

Figure 3:
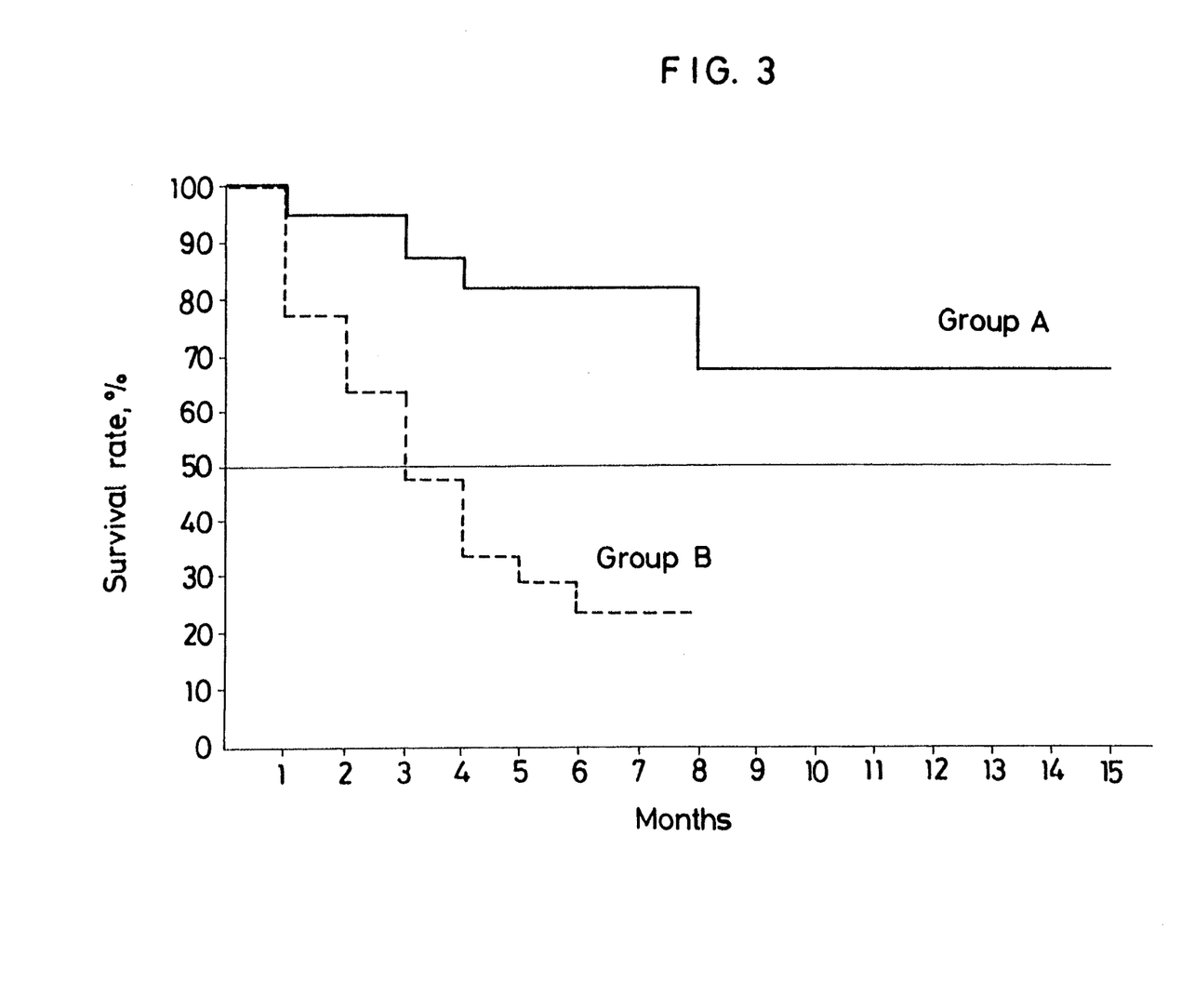
FIG. 3 diagrammatically shows relationship between G/L ratio and the prognoses of cancer patients.

FIG. 3 illustrates results of a comparison on survival curves determined by Kaplan-Meier method ["Chiryo Koka Hantei no tameno Jitsuyo Tokeigaku (Practical Statistics for Judgement of Therapeutic Effects)", Suketami Tominaga, Kani Shobo, published Aug. 20, 1982].

In FIG. 3, survival rates (%) are plotted along the axis of ordinates while time periods passed are plotted in terms of months along the axis of abscissas.

It is clearly envisaged from the diagram that the survival rate of Group A is higher with a significant difference and the prognosis of Group A is better.

EXAMPLE 4

Cases:

In the following cases, the respective patients were all treated by the same conventional immunotherapy and were not subjected to any other treatment except for the radiotherapy indicated specifically.

The G/L ratios of the patients in the respective cases were determined. Results are diagrammatically shown in FIG. 4 to FIG. 10 respectively, in each of which G/L ratios are plotted along the axis of ordinates while the days passed are plotted along the axis of abscissas.

Figure 4:
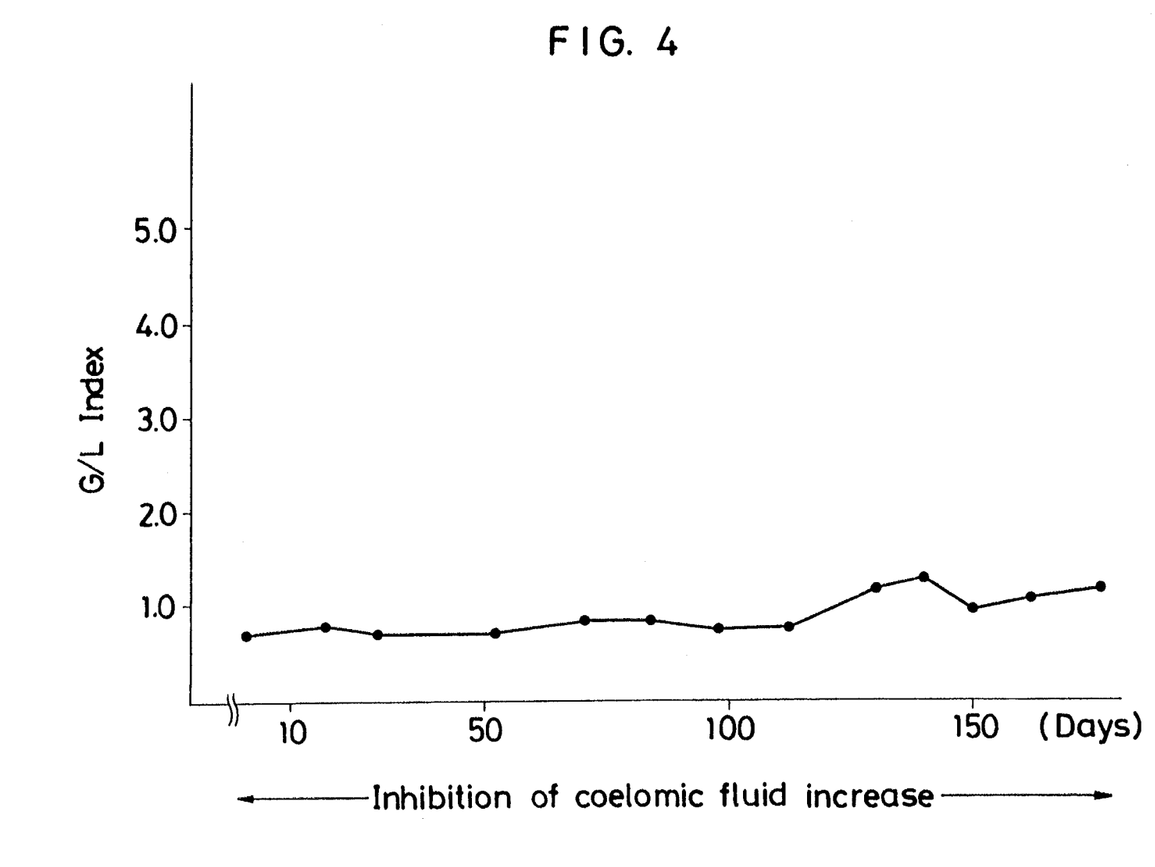
FIG. 4 through FIG. 10 diagrammatically depict changes in G/L ratio of Case 1 through Case 7 respectively.

Case 1: FIG. 4

S.S., 59 years old, male, case after the resection of uncured gastric cancer.

Although pool of ascitic fluid due to peritonitis carcinomatosa was observed right after the operation, the G/L ratio remained within the normal range and good therapeutic effects such as inhibition of coelomic fluid increase was observed. The general condition was in remission, so that his treatment has been continued as an outpatient.

Figure 5:
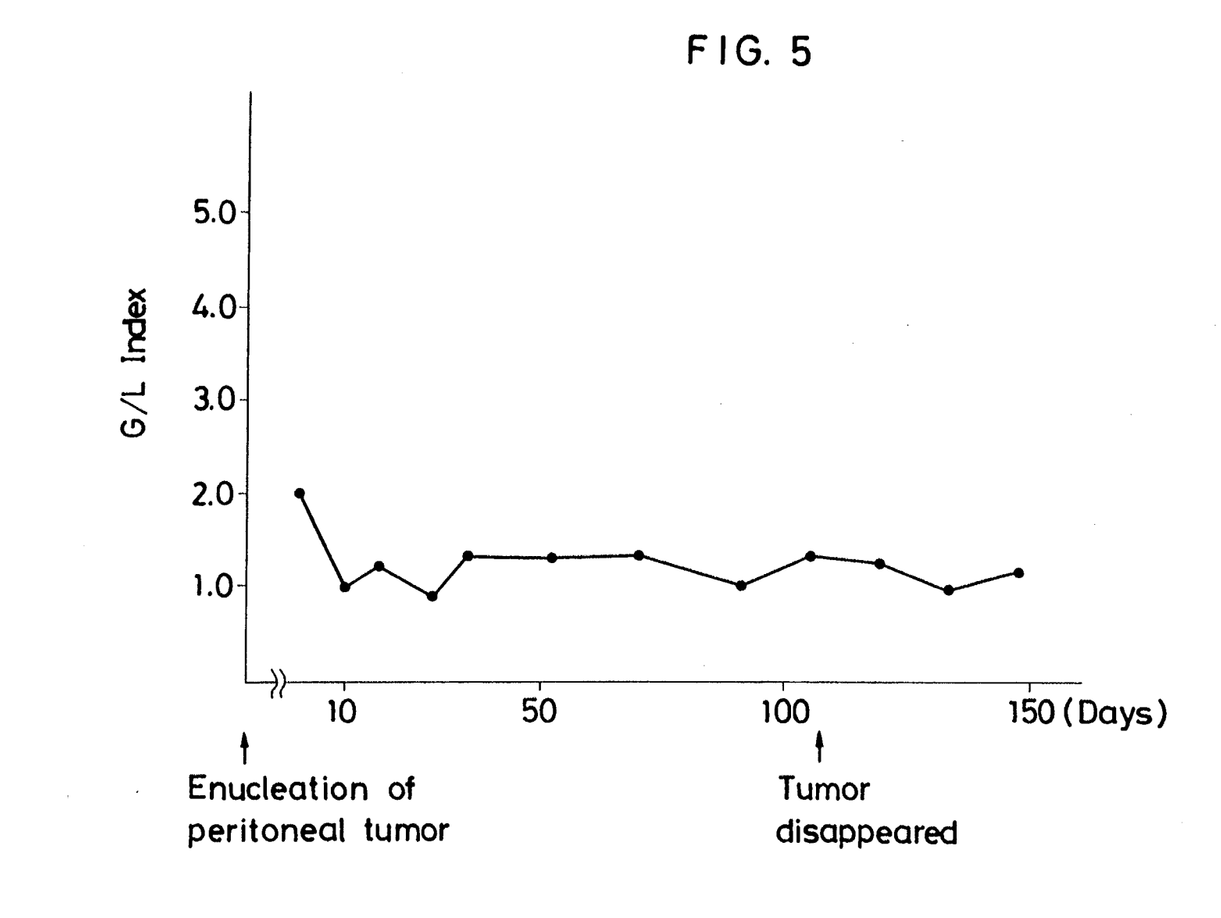

Case 2: FIG. 5

C.K., 64 years old, male, case of postoperative recidivation of small intestinal leiomyoma (intraabdominal and intraperitoneal metastasis).

After enucleation of peritoneal tumor, the G/L ratio remained within the normal range. Abdominal tumor was inoperable and was left over. Disappearance of the tumor was however observed on the 107th day after the initiation of the postoperative treatment. The general condition was in remission, so that his treatment has been continued as an outpatient.

Figure 6:
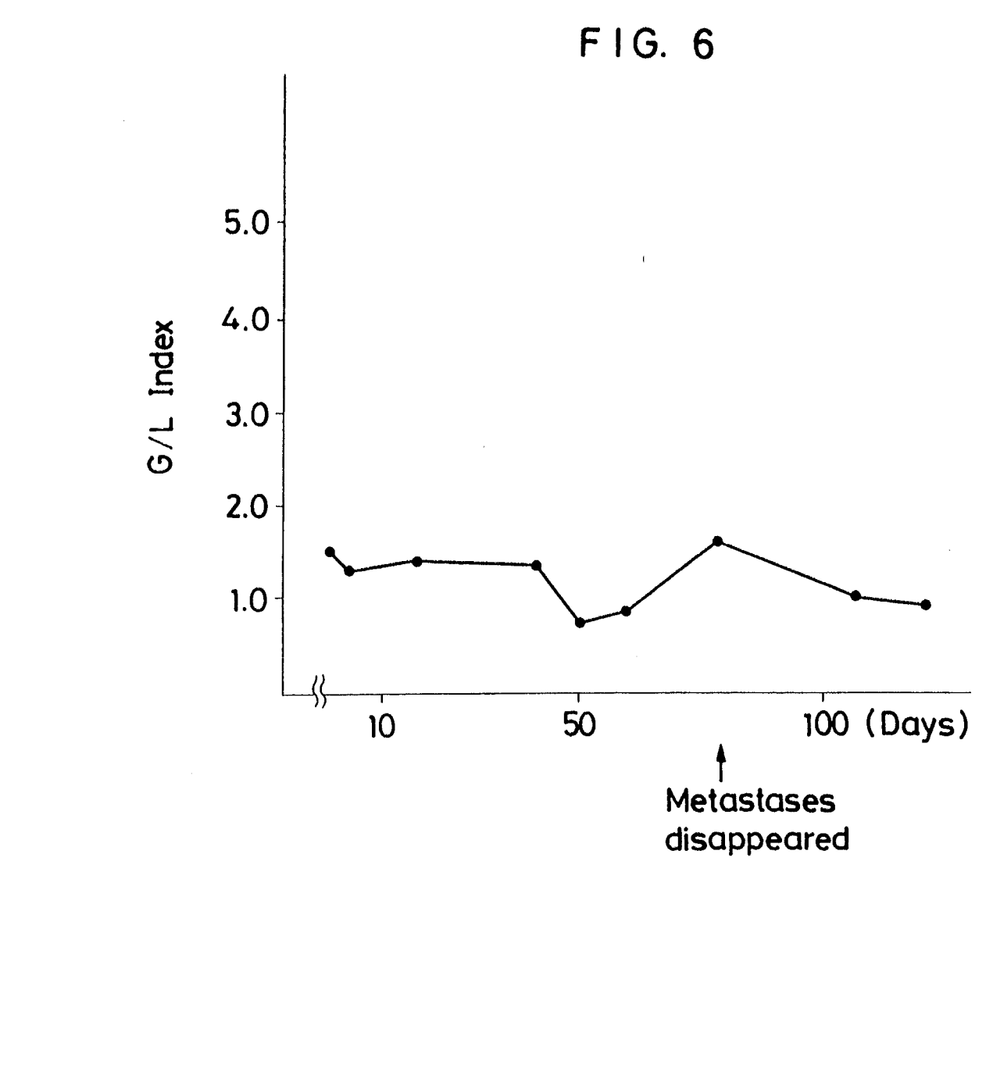

Case 3: FIG. 6

K.S., 64 years old, female, case of cutaneous metastasis after operation of mastocarcinoma.

The G/L ratio remained within the normal range, and on the 86th day after the commencement of the treatment of cutaneous metastases, disappearance of the cutaneous metastases was observed. Further, the general condition was in remission, so that her treatment has been continued as an outpatient.

Figure 7:
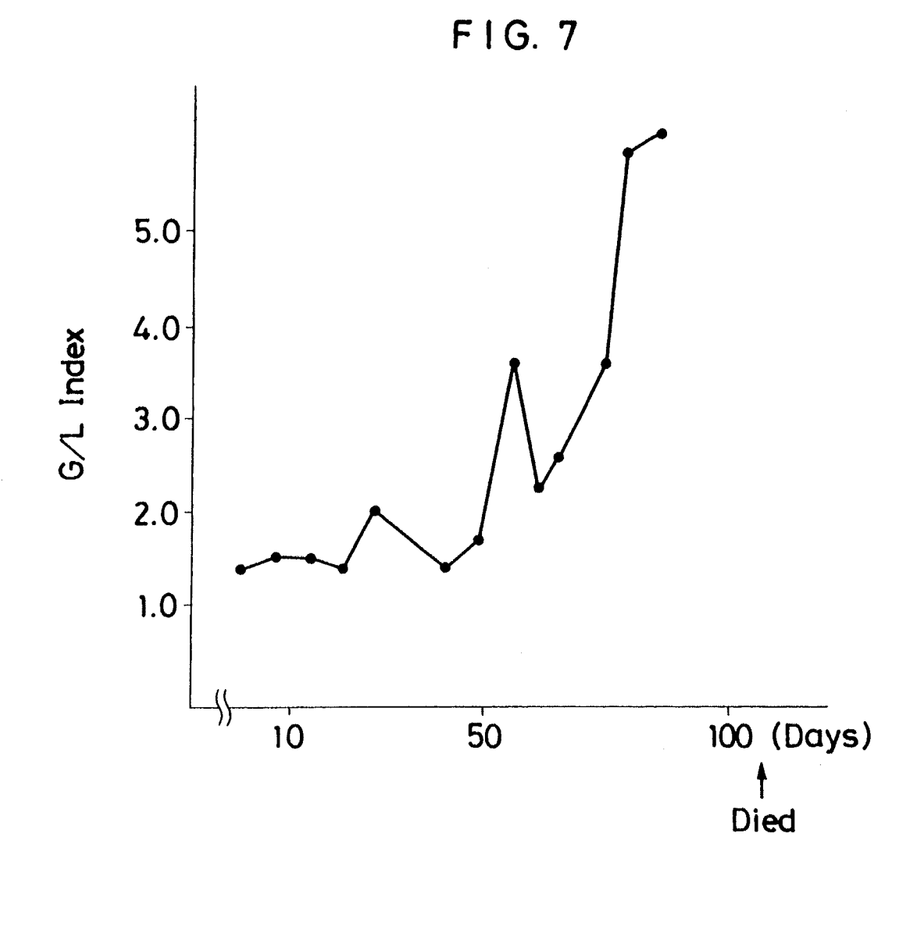

Case 4: FIG. 7

H.S., 68 years old, male, case of resection of uncured gastric cancers.

The G/L ratio increased and at the same time, the general condition was deteriorated. He died on the 108th day after the initiation of the postoperative treatment.

Figure 8:
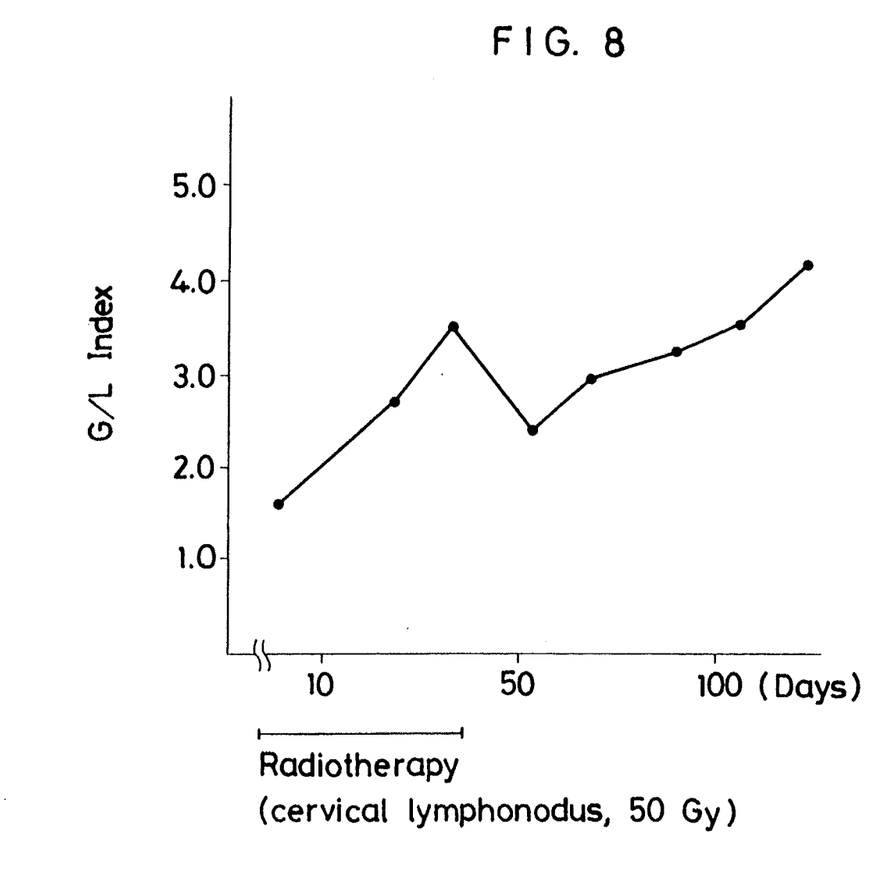

Case 5: FIG. 8

A.T., 57 years old, female, case of recidivation after radiotherapy of uterocervical cancer (metastasis to lungs and cervical lumphonodus).

In spite of application of radiotherapy from the 0th day to 40th day (cervical lymphonodus, 50Gy), deterioration of lung metastases and that of the general condition were observed.

Figure 9:
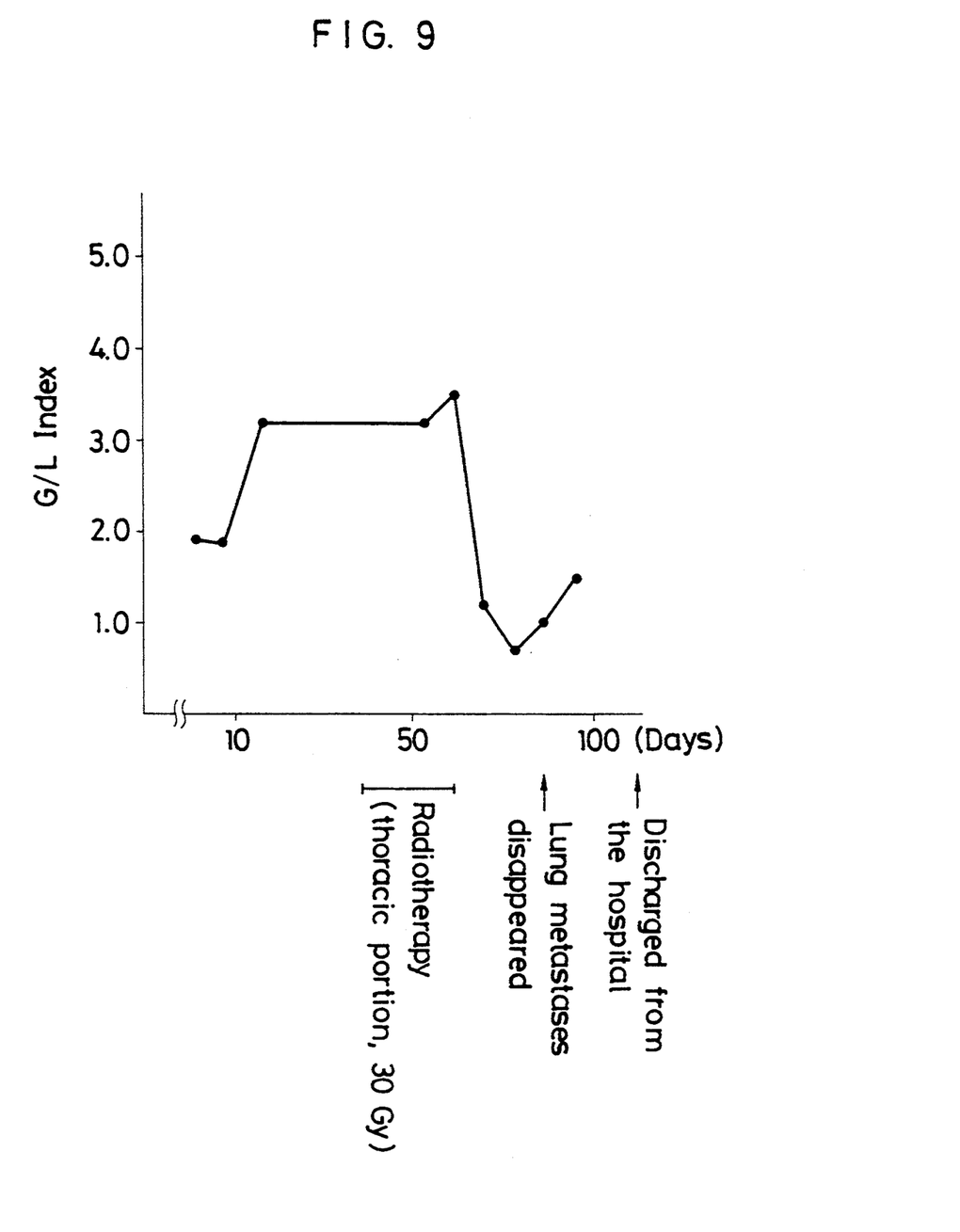

Case 6: FIG. 9

M.S., 43 years old, female, case of recidivation after operation of cancer of the left breast (metastasis to liver, thoracic portion and lungs).

The G/L ratio was high and no therapeutic effects were observed. Radiotherapy was applied further during the 35th day–60th day (thoracic portion, 30Gy). Along with improvements in the G/L ratio, the general condition was brought into remission and disappearance of lung metastases was observed. She was discharged on the 100th day from the hospital. Her treatment has been continued as an outpatient since then.

Figure 10:
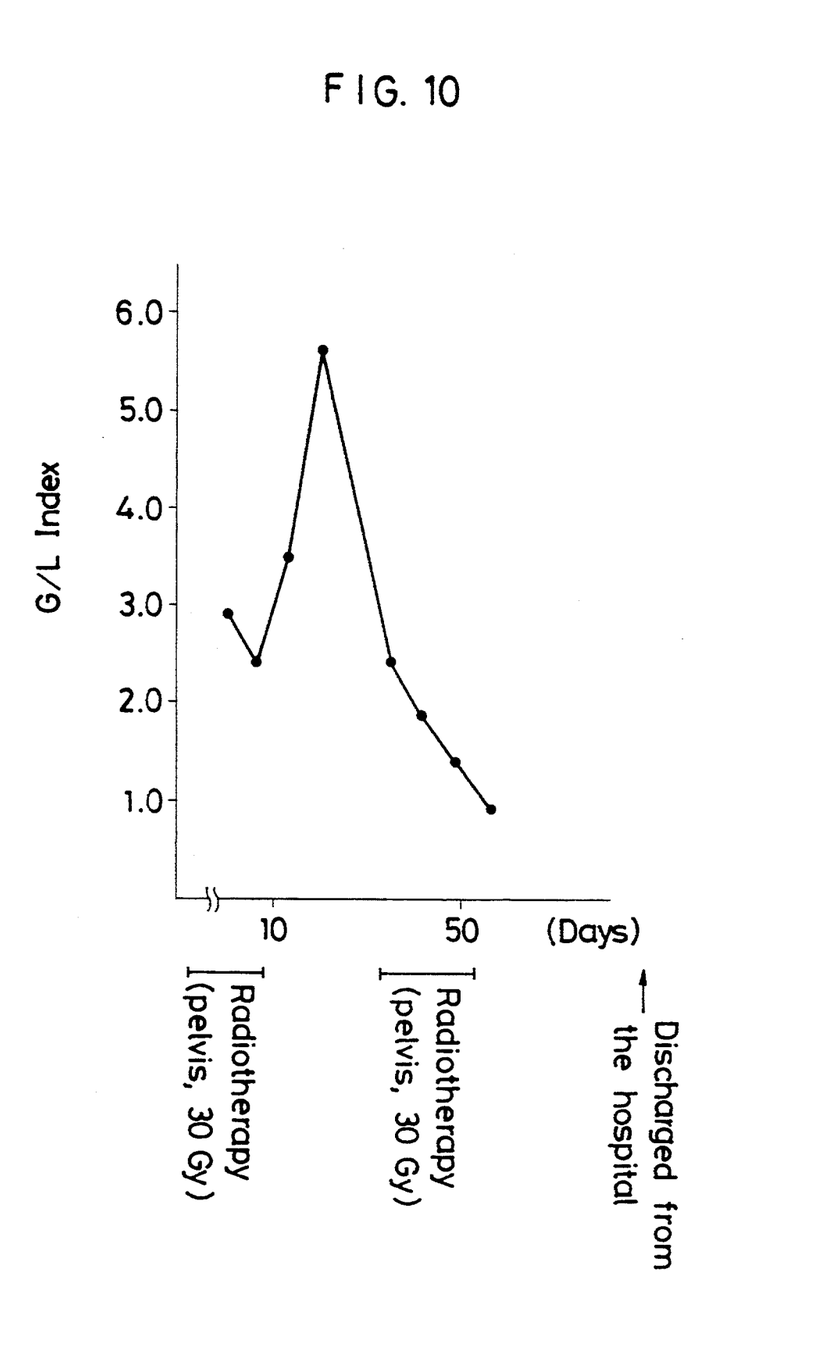

Case 7: FIG. 10

F.H., 70 years old, female, IV-stage uterine cancer.

Metastasis to the ureter and retroperitoneal lumphoglandula was observed. The general condition was poor, and no therapeutic effects was observed even by radiotherapy (pelvis, 30Gy). Improvements in the G/L ratio were however observed from the 35th day. After parallel application of radiotherapy (pelvis, 20 Gy) during the 35th day–55th day, significant improvements in the general condition were observed. She was discharged on the 85th day from the hospital. She was then able to receive treatments as an outpatient.

EXAMPLE 5

Test on the removal of granulocytes by using beads.

Employed as beads were polystyrene beads produced by polishing after their injection molding [diameter: 1.0 mm ("PSB-1"; product of Sekisui Chemical Co., Ltd.); or 3.5 mm ("PSB-2"; product of Sekisui Chemical Co., Ltd.)].

1.5 ml of "PSB-1" and 50 beads of "PSB-2" were separately placed in test tubes. To each test tube was added 1.5 ml of blood. The blood had been collected from a normal subject under heparinization. Each tube was shaken at room temperature for 2 hours.

G/L ratios after the adsorption treatment with the above beads are shown in Table 2.

TABLE 2

| | G ($\times 10^{-2}$/mm$^3$) | L ($\times 10^{-2}$/mm$^3$) | G/L ratio |
|---|---|---|---|
| Before treatment | 47 | 28 | 1.7 |
| After treatment with "PSB-1" | 20 | 32 | 0.6 |
| After treatment with "PSB-2" | 23 | 29 | 0.8 |

It is understood from Table 2 that granulocytes are efficiently adsorbed by the above treatment and blood having a lowered G/L ratio can be obtained. Incidentally, evaluation was also performed in the above test by observing smear (200 cells in total). The proportion of neutrophils was found to decrease, in other words, the corresponding increase of the proportion of lymphocytes was observed. The substantial reduction of the G/L ratio was also confirmed.

From the above test results, it is clearly envisaged the usefulness of the granulocyte removing apparatus of this invention for the improvement of an abnormally-high G/L ratio of a cancer patient. In addition, such improvements in the G/L ratio are extremely useful for the treatment of a cancer as readily understood from the cases reported above.

EXAMPLE 6

Test on the removal of granulocytes by using beads.

Polystyrene beads, polytrifluoroethylene beads, 6-nylon beads, cellulose acetate beads and polyethylene terephthalate beads, all of which were products of Sekisui Chemical Co., Ltd., had been produced by polishing subsequent to their injection molding and had a diameter of 3.2 mm. Glass beads were produced by melt forming (diameter: 3.2 mm) and used as beads.

About 5,000 beads of each type were immersed for 30 minutes in 500 ml of an aqueous solution which contained 5% of a surface active agent ("SCAT 20X-N", trade name; product of Dai-ichi Kogyo Seiyaku Co., Ltd.). They were then washed 5 times with deionized water and twice with 99.5% ethanol. The beads were dried in air and were finally exposed to gamma rays of 2.5 megarads in total, whereby the beads were washed and sterilized.

Fifty pieces of the above beads were placed in each of syringes whose capacities were 5 ml. 1.5 ml of bloods sampled from various cancer patients under heparinization was added to each syringe, followed by shaking or reaction at 37° C. for 30 minutes.

The bloods were thereafter separately transferred into test tubes, and their white blood cells and granulocytes were counted. Results are summarized in Table 3.

TABLE 3

| | Esophageal carcinoma patient (anaphase) K.F. | | Gastric cancer (anaphase) T.O. | | Postoperative patient of colonic cancer S.S. | | Chronic gastritis patient K.M. | |
|---|---|---|---|---|---|---|---|---|
| | G/L | # of G/mm$^3$ | G/L | # of G/mm$^3$ | G/L | # of G/mm$^3$ | G/L | # of G/mm$^3$ |
| Control | 9.4 | 10300 | 5.1 | 7100 | 2.0 | 7300 | 1.5 | 4100 |
| Polystyrene | 4.5 | 6700 | 4.0 | 5500 | 1.9 | 6000 | 1.1 | 3000 |
| Polytrifluoroethylene | 7.3 | 6600 | 4.4 | 6200 | 1.4 | 5300 | 1.1 | 3000 |

TABLE 3-continued

|  | Esophageal carcinoma patient (anaphase) K.F. | | Gastric cancer (anaphase) T.O. | | Postoperative patient of colonic cancer S.S. | | Chronic gastritis patient K.M. | |
| --- | --- | --- | --- | --- | --- | --- | --- | --- |
|  | G/L | # of G/mm³ | G/L | # of G/mm³ | G/L | # of G/mm³ | G/L | # of G/mm³ |
| Glass | 6.5 | 6500 | 4.5 | 7100 | 1.5 | 6400 | 1.5 | 4100 |
| 6-Nylon | 8.0 | 5600 | 5.1 | 6100 | 1.6 | 5800 | 1.1 | 3100 |
| Cellulose acetate | 1.6 | 3100 | 2.9 | 5500 | 0.7 | 3000 | 0.6 | 1800 |
| Polyethylene terephthalate | 5.5 | 6100 | 4.5 | 6400 | 1.8 | 6700 | 1.1 | 3100 |

In the above test, evaluation was also made by observing smear (200 cells in total). Results were similar to those obtained by the above instrument.

EXAMPLE 7

Experiment on the removal of granulocytes by in vivo external circulation

In order to demonstrate effects of the granulocyte removing apparatus according to this invention by in vivo external circulation, a granulocyte removal experiment was conducted under external circulation by using two 3-years old 11-kg heavy beagle dogs, one being female and the other male.

Employed as a granulocyte removing portion was a column having an inner diameter of 3 cm, a height of 10 cm and an internal capacity of 71 ml. About 2,550 cellulose acetate beads (diameter: 3.2 mm; product of Sekisui Chemical Co., Ltd.), which had been produced by polishing after their injection molding, were washed and sterilized in the same manner as in Example 6. The beads were then packed in the column. After the packing of the beads, the blood volume inside the column was about 28 ml. An external circulation system was constructed by exsanguination tubes in such a way that blood was taken directly from the inguinal artery, fed to the granulocyte adsorbing portion and then returned to the inguinal vein. The flow velocity was controlled at 100 ml/min by an external circulation pump. Further, before feeding the blood to the column, heparine was mixed as an anticoagulant at a rate of 1000 U/hr to the blood. In addition, protamine was also mixed as a heparine antagonist to the blood which had passed through the column.

Sampling of blood was conducted directly from the carotid both before and after the external circulation. During the external circulation, the blood was sampled through connection tubes both upstream and downstream of the column. Using these blood samples, G/L ratios were determined. Results are shown in Table 4.

TABLE 4

| Removal time of granulocytes (min) | 0 | 5 | 10 | 20 | 30 | 45 |
| --- | --- | --- | --- | --- | --- | --- |
| Beagle 1 | 3.0 | 1.9 | 2.3 | 1.8 | 2.1 | 0.8 |
| Beagle 2 | 3.3 | 0.8 | 1.0 | 1.0 | 1.5 | 1.2 |

It is clear from these results that cellulose acetate, polystyrene and the like out of these beads materials can lower the G/L ratio effectively and even when externally circulated in vivo, cellulose acetate beads can effectively lower the G/L ratio and shows clinical effectiveness.

We claim:

1. A method of assessing prognosis of a patient undergoing therapy for cancer, which comprises:
   a) measuring a granulocyte/lymphocyte ratio (G/L ratio) of said patient; and
   b) comparing said measured G/L ratio in said cancer patient with a G/L ratio range of 1.6±0.6, in order to determine whether the G/L ratio of said patient is within said range or greater,
   whereby prognosis of said patient is indicated as being improved when said measured G/L value is within said range as compared to when said measured G/L valve is greater than said range of 1.6±0.6.

* * * * *

UNITED STATES PATENT AND TRADEMARK OFFICE
CERTIFICATE OF CORRECTION

PATENT NO. : 5,403,719

DATED : April 4, 1995

INVENTOR(S) : MASAKAZU ADACHI ET AL

It is certified that error appears in the above-identified patent and that said Letters Patent is hereby corrected as shown below:

Column 10, line 42, "valve" should read -- value --.

Signed and Sealed this

Seventh Day of November, 1995

Attest:

BRUCE LEHMAN

*Attesting Officer*     *Commissioner of Patents and Trademarks*